United States Patent
Tanaami et al.

(10) Patent No.: US 7,384,780 B2
(45) Date of Patent: Jun. 10, 2008

(54) HYBRIDIZATION METHOD AND HYBRIDIZATION EQUIPMENT

(75) Inventors: Takeo Tanaami, Musashino (JP); Hisao Katakura, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 146 days.

(21) Appl. No.: 10/730,061

(22) Filed: Dec. 9, 2003

(65) Prior Publication Data

US 2004/0115723 A1 Jun. 17, 2004

(30) Foreign Application Priority Data

Dec. 11, 2002 (JP) ............... 2002-359034

(51) Int. Cl.
*C12M 1/34* (2006.01)
*G01N 27/447* (2006.01)
(52) U.S. Cl. ............... 435/287.2; 435/285.2; 435/287.9; 204/403.01; 204/606; 204/643
(58) Field of Classification Search ............ 435/287.2, 435/287.9, 285.2; 204/606, 643, 403.01
See application file for complete search history.

(56) References Cited

U.S. PATENT DOCUMENTS 5,789,167 A * 8/1998 Konrad ............... 435/6
2001/0005718 A1* 6/2001 Wen-Tung et al. ............ 514/44

2003/0087292 A1* 5/2003 Chen et al. ............... 435/6

FOREIGN PATENT DOCUMENTS

| JP | 2000-105218 | 4/2000 |
| JP | 2002-85095 | 3/2002 |
| JP | 2003-527601 | 9/2003 |
| WO | WO 01/69230 A2 | 9/2001 |

OTHER PUBLICATIONS

Michael J. Heller, IEEE Engineering in Medicine and Biology, pp. 100-104; Mar./Apr. 1996.

* cited by examiner

*Primary Examiner*—William H Beisner
(74) *Attorney, Agent, or Firm*—Westerman, Hattori, Daniels & Adrian, LLP.

(57) ABSTRACT

The equipment of the present invention can implement high-speed hybridization with a simple construction and is configured as described below.

The equipment comprises a biochip prepared by fixing biopolymers onto a plurality of sites on a substrate, positive and negative electrodes for generating an electric field along the surface of this biochip substrate, and a magnetic field generating means for generating a magnetic field along the surface of the above biochip substrate, and is configured to move biopolymers movable in the fluid stored over the above-mentioned biochip substrate along the surface of the above biochip substrate as well as to attract the above described biopolymers towards the surface of the above biochip substrate during hybridization of the above biopolymers, by making the above-mentioned electric and magnetic fields act along the surface of the above biochip substrate.

8 Claims, 7 Drawing Sheets

Side view

Front view

HYBRIDIZATION METHOD AND HYBRIDIZATION EQUIPMENT

BACKGROUND OF THE INVENTION

1. Field of the Invention

The present invention relates to a hybridization method and hybridization equipment for achieving higher speed and higher efficiency hybridization for biopolymers such as deoxyribonucleic acid (hereafter called DNA), or ribonucleic acid (hereafter called RNA) or proteins attached to DNA, RNA, or the like.

2. Description of the Prior Art

In measuring gene sequences of biopolymers such as DNA, RNA, or proteins attached to RNA or DNA, or the like, DNA chips for hybridization have been used until now.

DNA chips used for hybridization include the one constructed such that multiple electrodes are provided on a substrate and a current source is connected to each electrode, as mentioned, for example, in Michael J. Heller, "An Active Microelectronics Device for Multiplex DNA Analysis," IEEE Engineering in Medicine and Biology Magazine, 1996, March/April, pp.P100-101. The number of electrodes is about 100 to 10000 and, in general, known different DNAs are fixed to each electrode.

By causing hybridization by passing unknown DNA on a substrate on which such known DNAs are fixed, the unknown DNA is bonded to corresponding DNA sequences. If a fluorescent reagent is bonded to unknown DNA in advance, the sequence of the unknown DNA bonded to known DNA can be known.

The above will be further described in detail below. As shown in FIG. 1(a), a positive voltage is applied to an electrode 81 on which known DNA 82 is fixed. A solution in which unknown DNA 83 can flow is stored (not shown in the drawing) in a region on electrode 81. Unknown DNA 83 is negatively charged and attracted to electrode 81, to which DNA 82 is fixed, moving in the solution as shown in FIG. 1(b). This action increases the concentration of unknown DNA 83 around electrode 81, thus increasing the speed of hybridization.

In addition, if known and unknown DNAs are bonded causing sequence mismatching by mistake, this bonding can be cut off by applying a slight negative voltage to electrode 81 on the contrary after hybridization as shown in FIG. 2(b). As a result, a difference of only one base such as for single nucleotide polymorphisms (SNPs) can be measured with high precision.

However, such conventional method has the following problems:

(1) The method requires individual electrodes to be provided for every site on a DNA chip. This is expensive as well as complicated in construction and it is necessary to ensure wide electrode spaces. Accordingly, this method cannot increase the number of sites and the site pattern on the chip has less degree of freedom.

(2) If a kind of unnecessary DNA having a sequence different from that of the known DNA is once gathered to a site, it is bonded to the known DNA but defectively. For example, as shown in FIG. 3, assume that both unknown DNA (A2) and unknown DNA (B2) are gathered to site A on which known DNA (A1: not shown in the drawing) is fixed. Then, if known DNA (A1) bonded with unknown DNA (A2) causes the appropriate hybridization, unknown DNA (B2) is unnecessary for site A.

On the other hand, assume that both unknown DNA (B2) and unknown DNA (A2) are gathered to site B on which known DNA (B1: not shown in the drawing) is fixed. Then, if known DNA (B1) bonded with unknown DNA (B2) causes the appropriate hybridization, unknown DNA (A2) is unnecessary for site B.

SUMMARY OF THE INVENTION

The present invention is intended to solve the above-described problems; the objective is to provide a high-speed and high-precision hybridization method in which high-speed hybridization can be implemented using a simple construction and to offer hybridization equipment in which the above method is realized.

In addition, another objective of the present invention is to offer a hybridization method which can improve the possibility of each biopolymer encountering correct sites, that is, to improve the hybridization efficiency and to provide hybridization equipment in which the above method is realized.

BRIEF DESCRIPTION OF THE DRAWINGS

FIG. 1 is a drawing showing an example of conventional DNA chips for hybridization.

FIG. 2 is a drawing describing the state of changing over a voltage applied to the electrode at a conventional DNA chip.

FIG. 3 is a drawing illustrating incomplete bonding.

FIG. 4 is a configuration drawing showing the hybridization equipment of an embodiment of the present invention.

FIG. 5 is a drawing indicating the arrangement of magnets and electrodes.

FIG. 6 is a drawing illustrating forces acting on target DNA.

FIG. 7 is a drawing showing electrodes of another embodiment of the present invention.

FIG. 8 is a drawing showing electrodes of another embodiment of the present invention.

FIG. 9 is a drawing showing electrodes of another embodiment of the present invention.

FIG. 10 is a drawing showing electrodes of another embodiment of the present invention.

FIG. 11 is a drawing showing electrodes of another embodiment of the present invention.

FIG. 12 is a drawing showing a method of applying a magnetic field as another embodiment of the present invention.

FIG. 13 is a drawing showing the electrode portion as another embodiment of the present invention.

DETAILED DESCRIPTION OF THE PREFERRED EMBODIMENTS

Figures 1A, 1B:
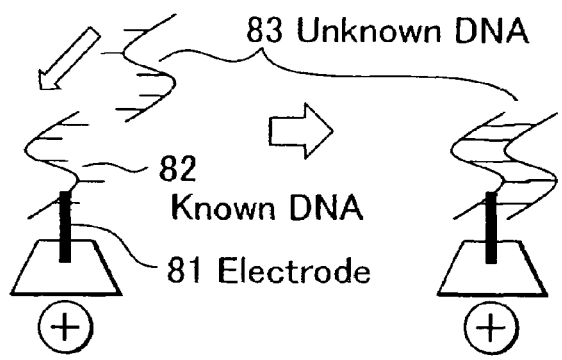
[FIG. 1]
Figures 2A, 2B:
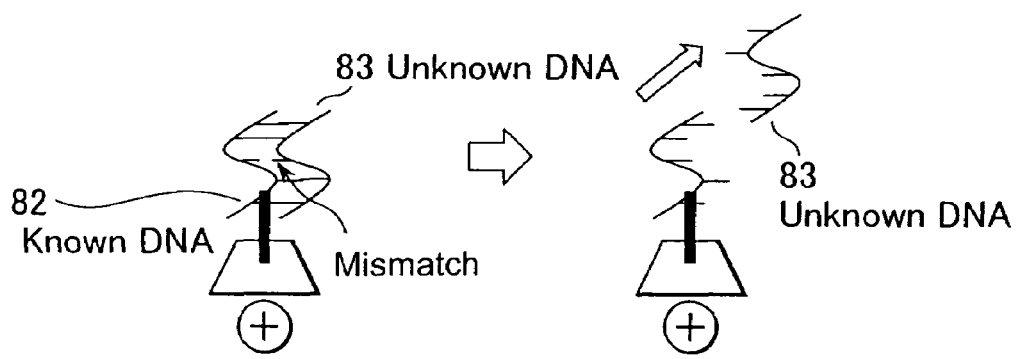
[FIG. 2]
Figure 3:
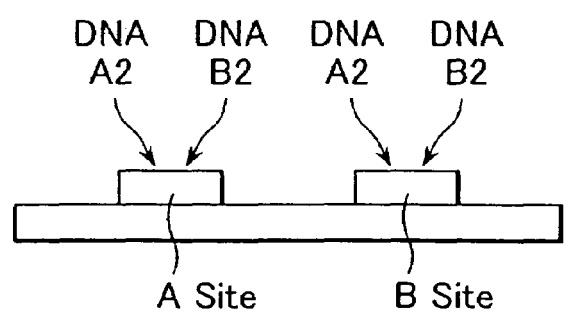
[FIG. 3]
Figure 4:
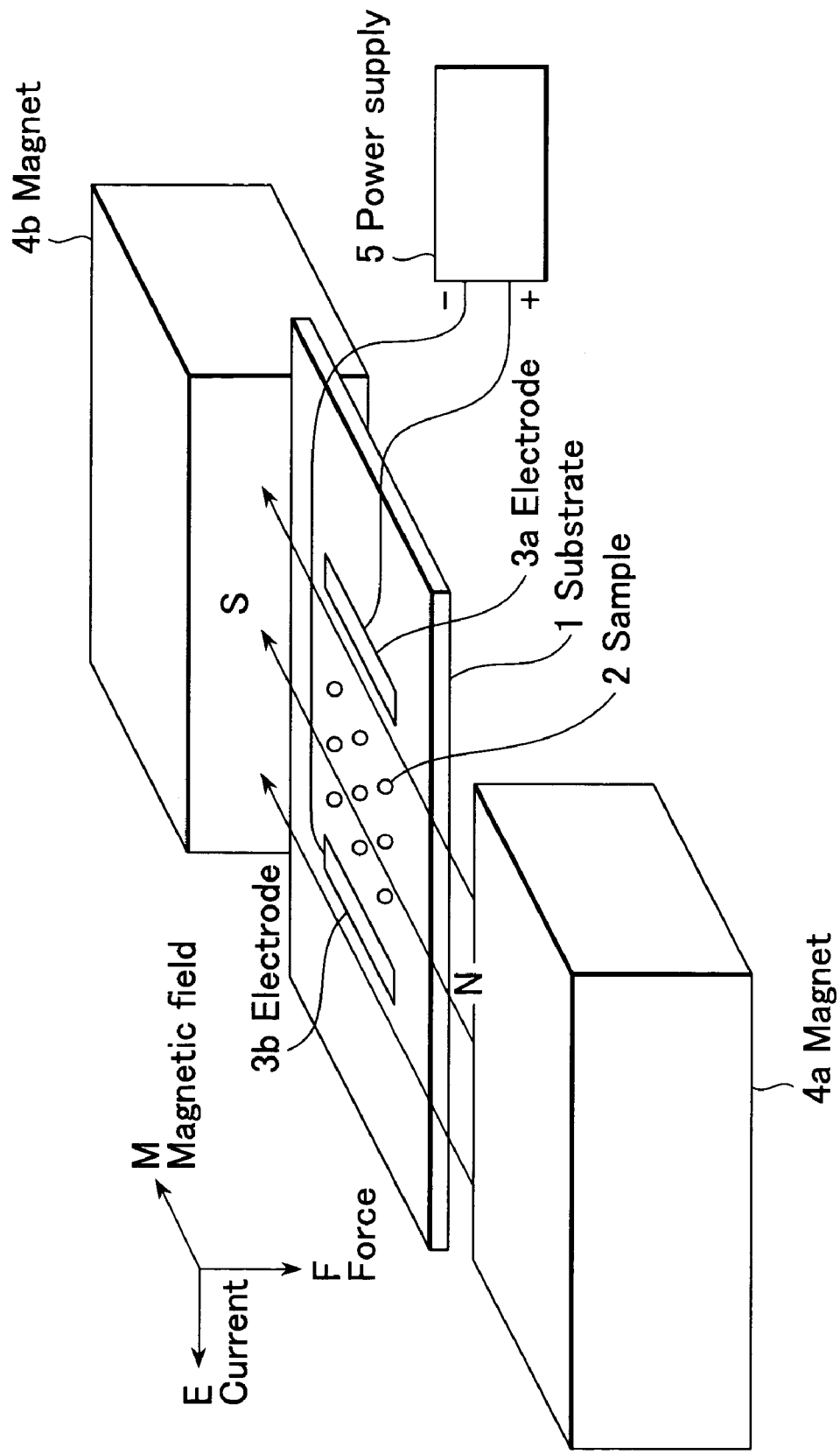
[FIG. 4]

The present invention will be described below in detail using the drawings. FIG. 4 is a configuration drawing showing the hybridization equipment of an embodiment of the present invention. In FIG. 4, numeral 1 shows a substrate and numeral 2 shows samples (biopolymers on the fixed side) fixed to a plurality of sites on substrate 1. Numerals 3a and 3b show electrodes mounted on substrate 1, numerals 4a and 4b show magnets as a means of generating a magnetic field, and numeral 5 a power supply for applying a DC voltage to electrodes 3a and 3b. In addition, electrodes 3a and 3b are fixed to the positions on both sides of the sites sandwiching the sites. Samples 2 are not fixed on these electrodes but are fixed on the sites sandwiched by electrodes 3a and 3b.

In a region over substrate 1, a construction for storing fluid e.g. solution or gel is employed (not shown in the drawing). This fluid contains biopolymers 21 movable in the fluid (biopolymers on the movable side).

In addition, for biopolymers 2 on the fixed side and biopolymers 21 on the movable side, they can be selected as the known biopolymers on either side and the unknown biopolymers on the other side. They can also be selected as the probe biopolymers on either side and the target biopolymers on the other side.

Further, in this embodiment, an example is described in which biopolymers 2 on the fixed side are known probe DNA 2 and biopolymers on the movable side are unknown target DNA 21.

Figure 5A:
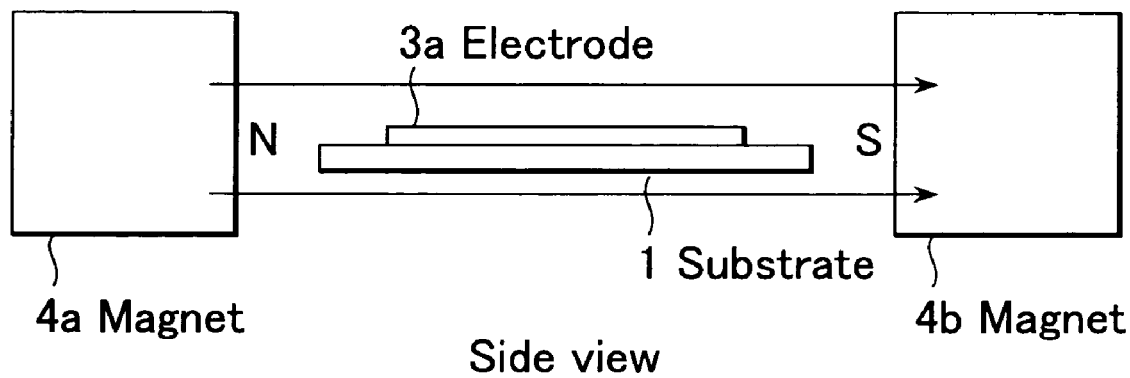
[FIG. 5]
Figure 5B:
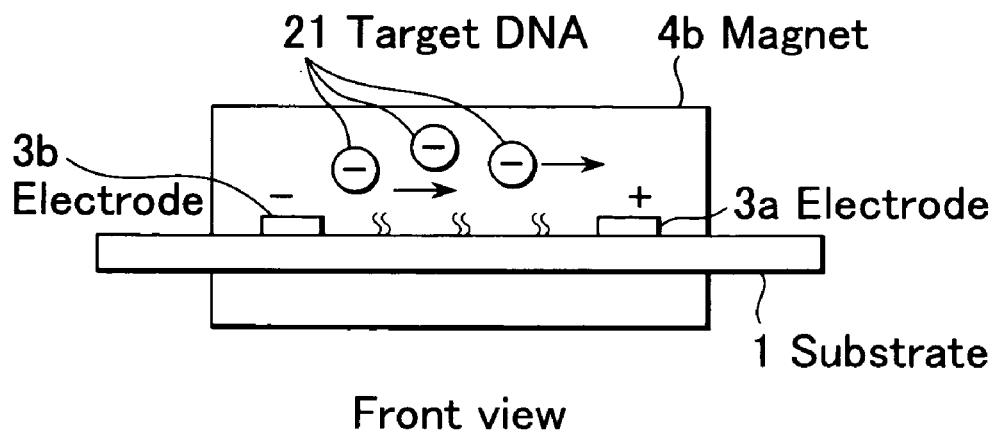

Magnets 4a and 4b are arranged so that poles N and S are counter to each other on both sides of the sites as shown in FIG. 5(a). Electrodes 3a and 3b are arranged on both sides of the sites as shown in FIG. 5(b). In this case, the direction of magnetic field generated by magnets 4a and 4b is orthogonal to the direction of electric field generated by electrodes 3a and 3b.

Figure 6:
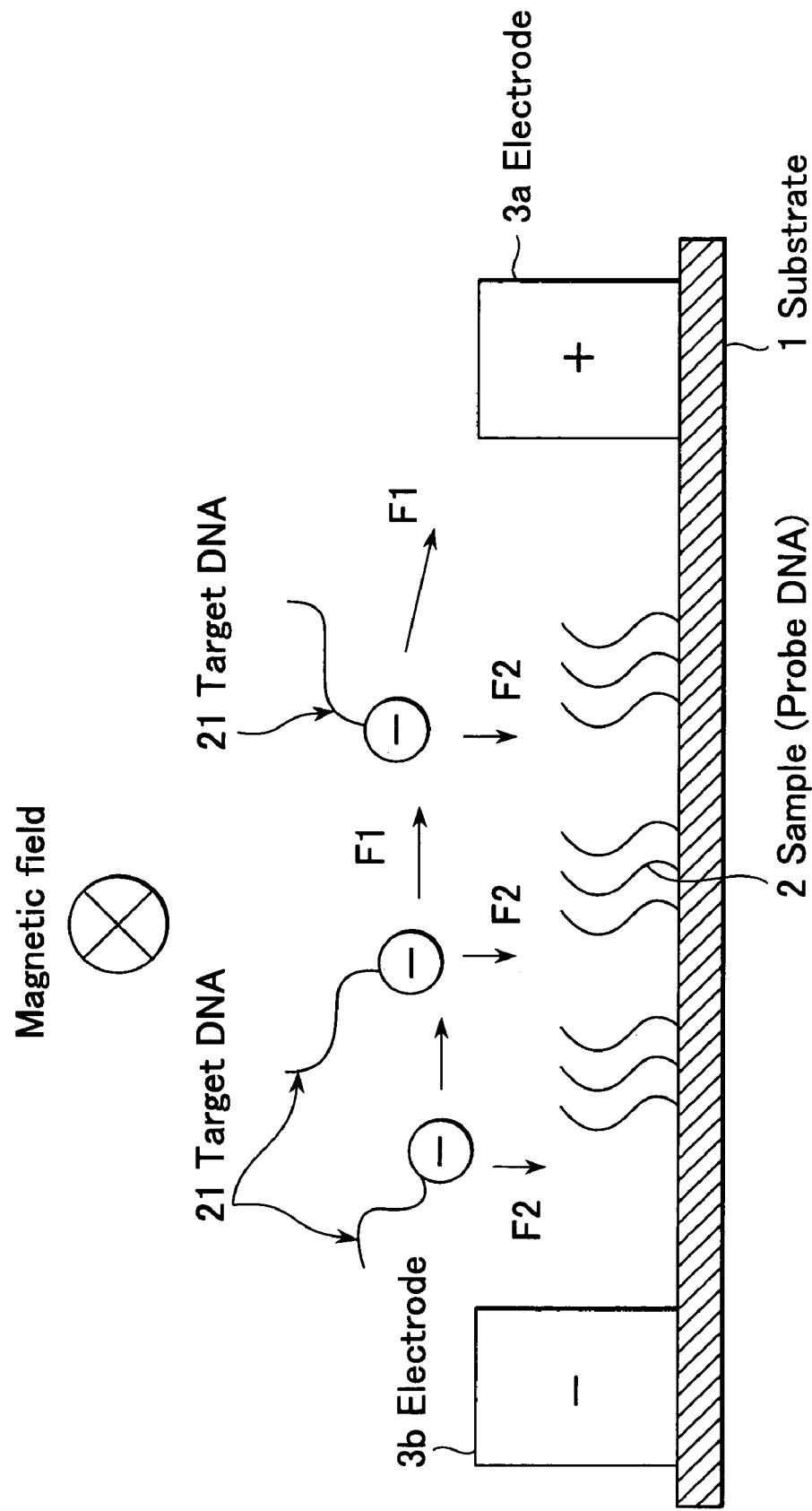
[FIG. 6]

In such a configuration, the region over substrate 1 is filled with a solution in which DNA 21 is mixed. The negatively charged target DNA moves through the solution and is attracted toward positive electrode 3a as shown in FIG. 6. Let this attractive force be $F_1$. In this case; target DNA 21 is subjected to force F2 toward the bottom of the drawing on the sheet as shown in FIG. 6 due to the current (movement of negatively charged target DNA is equivalent to the flow of electric current in the inverse direction) and the magnetic field B orthogonal to the direction of movement (the magnetic field in the direction toward the rear plane of the sheet from the front plane of the sheet), based on Fleming's left-hand rule.

This makes target DNA 21 in the solution be attracted towards the sites and thus the concentration of target DNA in the vicinity of the sites increases. For example, if target DNA 21 is attracted from the height of 20 μm over the sites before attraction to the height of 20 nm, target DNA 21 is compressed by 1000-fold and so the mixed DNA concentration increases by 1000-fold.

Further, since target DNA 21 is deflected on the positive electrode side if the solution is kept attracted toward the positive electrode, target DNA 21 is moved in the opposite direction again by reversing both the electric field and the magnetic field synchronously on the way (an already known mechanism for reversal can be used). This enables highly concentrated conditions of target DNA over each site to be achieved.

In addition, the present invention is not restricted to the above embodiment but may be embodied in other specific forms, changes, and versions without departing from the spirit or essential characteristics thereof. Such changes and versions are enumerated below.

(1) Although description is made for DNA as a sample in the above embodiment, the present invention can be applied widely to charged biopolymers such as DNA, RNA, protein attached to DNA or RNA, etc.

Figure 7:
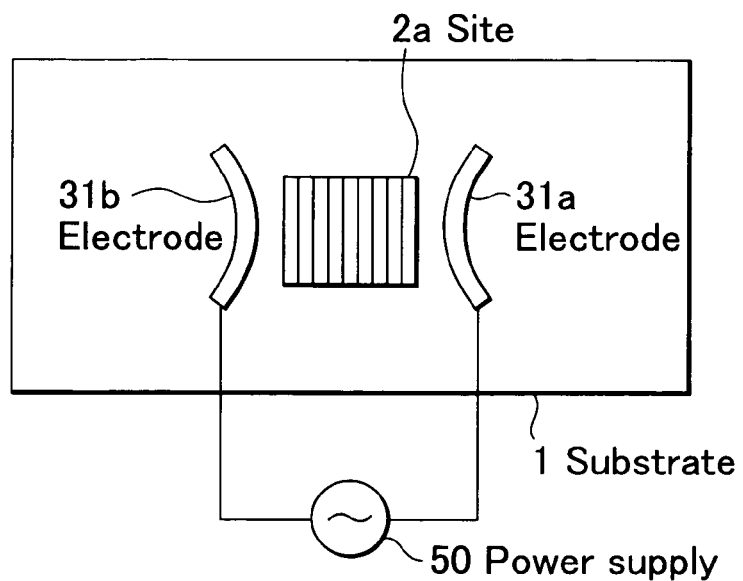
[FIG. 7]
Figure 8:
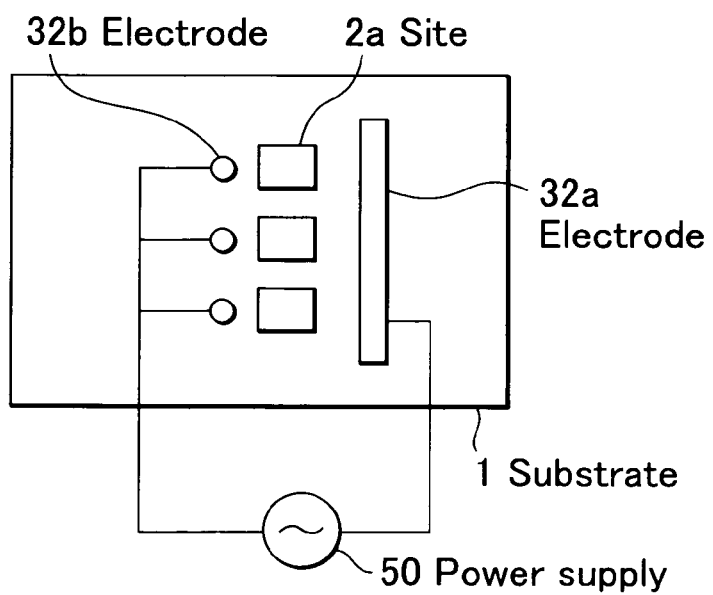
[FIG. 8]

(2) For example, the planar shape of electrodes may be bow-shaped bent backward against the sites as shown in FIG. 7 as electrodes 31a and 31b. Also, as shown in FIG. 8, a configuration, in which one of the two electrodes 32a is a straight-line common electrode while the other electrode 32b is composed of individual electrodes for each site, may be employed. The individual electrodes may be variously planar-shaped such as circular, ellipsoidal, rectangular, etc.

Figure 9:
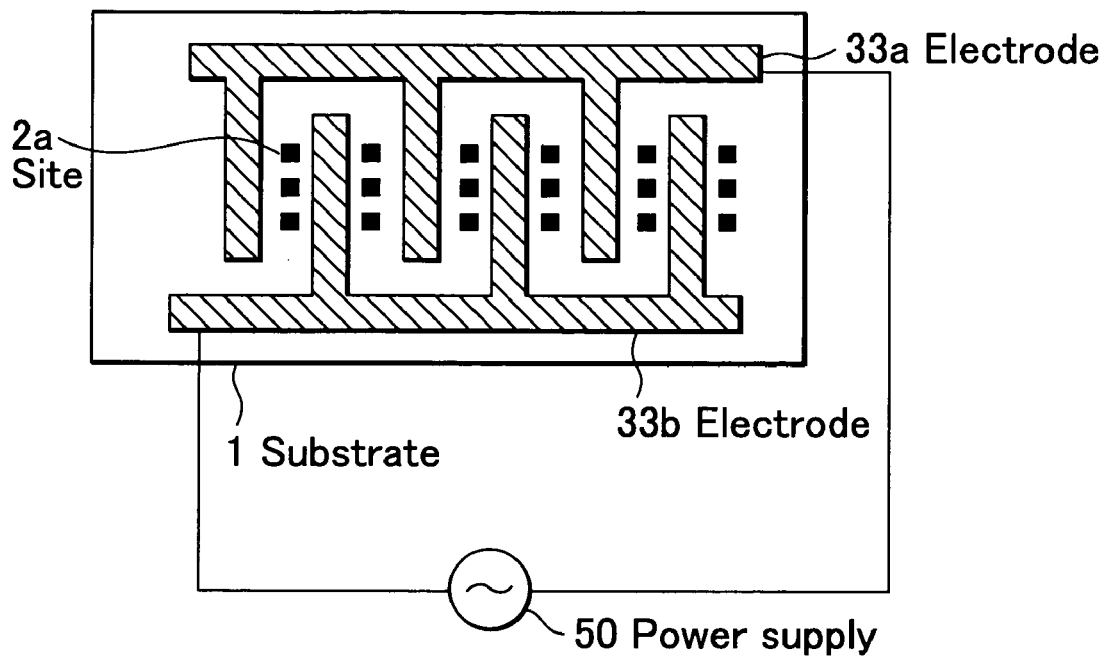
[FIG. 9]

Further, as shown in FIG. 9, the electrodes may be comb-teeth shaped so that sites are arranged between the comb-teeth of both electrodes.

Figure 10:
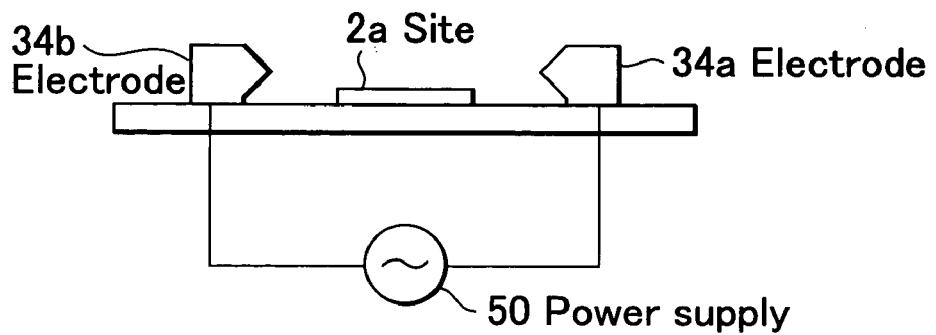
[FIG. 10]
Figure 11:
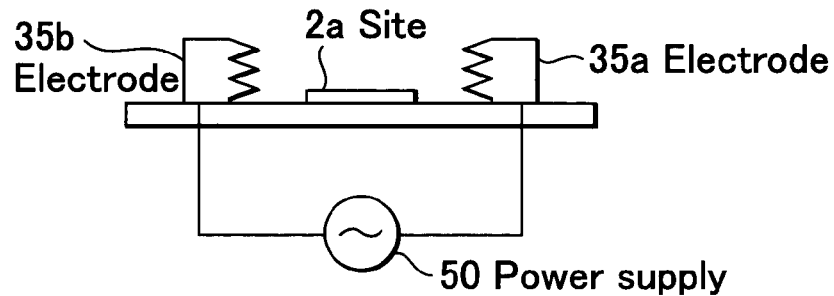
[FIG. 11]

Also, the shape of the cross section of the electrodes facing the sites may be triangular as shown in FIG. 10 or saw-teeth-like as shown in FIG. 11.

Incidentally, power supply 50 shown in FIG. 7 through FIG. 11 is an AC supply and generates an alternating electric field of predetermined period. Of course, there is no problem if power supply 50 is a DC supply.

Figure 12:
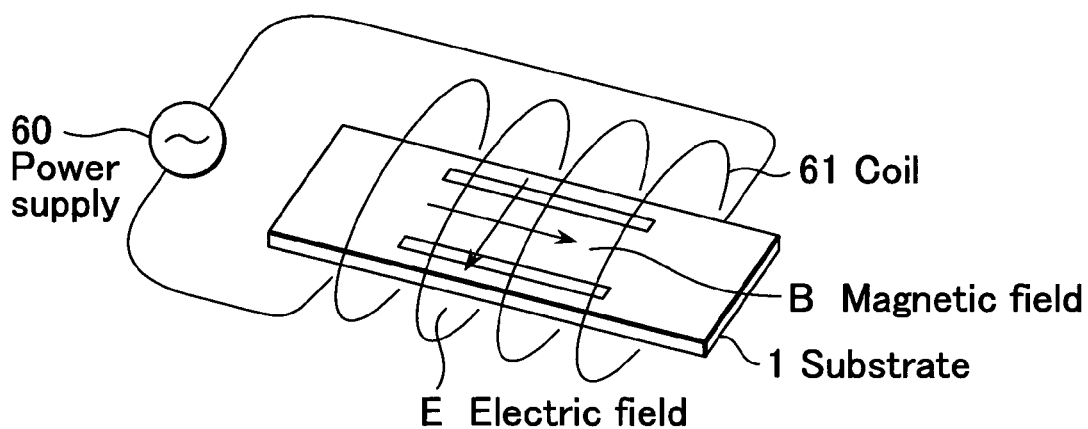
[FIG. 12]

Further, the magnetic field can be generated using a coil instead of magnets. FIG. 12 shows an example of a configuration in which DNA chips are arranged inside coil 61 and an alternating magnetic field is applied to DNA chips by driving coil 61 with AC power supply 60.

In the figures from FIG. 7 to FIG. 12, if the alternating periods of the magnetic and electric fields are synchronized, target DNA can be moved alternately in opposite directions over the substrate as described in the above embodiments. In order to achieve such magnetic field reversal using permanent magnets, it is sufficient to change the positions of magnets mechanically using a motor or motors.

Figure 13:
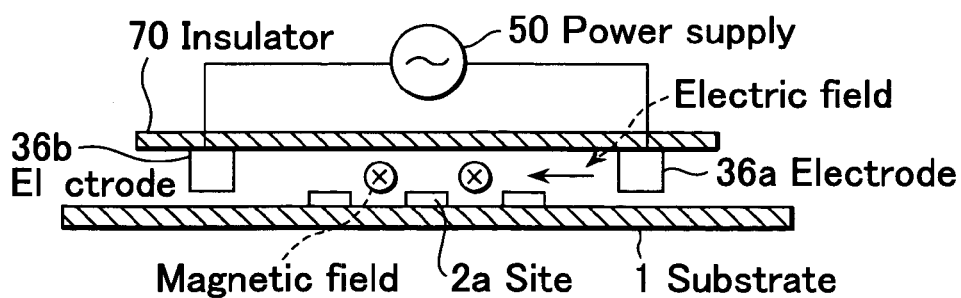
[FIG. 13]

(3) The electrodes may be separated from substrate 1 using a member for holding electrodes (not shown in the drawing) as shown in FIG. 13. It can be devised that an electric field is generated similar to the above-mentioned embodiment by attaching electrodes 36a and 36b to insulator 70 (for example, a cover glass that also serves as the lid of the enclosure in which the target DNA-mixed solution is stored).

(4) This method or equipment can be operated by applying only an electric field without a magnetic field. With this configuration, target DNA can be attracted towards an electrode and stirred. Therefore, reasonably high-speed hybridization becomes possible.

(5) In any embodiment, if the solution is changed to gel, the moving speed of the target DNA can be decreased.

(6) For electrodes, both metals and inorganic type materials such as carbon can be employed.

(7) The voltage should be a value at which bubbles due to electrolysis are not generated, for example 1.3 V or less.

(8) Substrate 1 may be made of wire or mesh, not a plate.

As described above, the following effects are achieved according to the present invention:

(1) Since the distribution of the target DNA in the vicinity of the probe DNA becomes highly concentrated, hybridization can be performed at a higher speed.

(2) Since a force to rip the hybridized DNA can also be generated by devising the application of the electric field and magnetic field, delicate mishybridization such as SNPs can be ripped.
(3) Since the electrodes are positioned on both sides of sites so that the sites are sandwiched by the electrodes, not in the position of each site as seen in conventional methods or equipment, the target DNA is not unevenly adsorbed into the probe DNA at the specific site. The target DNA can also be moved uniformly in the direction of site arrangement over the entire sites, and ineffective adsorption of target DNA is not generated.
(4) Since only a small number of electrodes is needed (at least two electrodes suffice) even if there are many sites, this method or equipment is cheap, compact and has a simple construction and also high reliability is assured.

What is claimed is:

1. Hybridization equipment comprising:
a biochip prepared by fixing biopolymers to a plurality of sites on a biochip substrate,
positive and negative electrodes for generating an electric field along the surface of said biochip substrate, and
a magnetic field generating means for generating a magnetic field along the surface of said biochip substrate;
wherein the electric and magnetic fields generated by said electrodes and said magnetic field generating means simultaneously act along the surface of said biochip substrate to move said biopolymers along the surface of said biochip substrate in a fluid stored over said biochip substrate and to attract said biopolymers towards the surface of said biochip substrate during hybridization of said biopolymers,
wherein said electric and magnetic fields are perpendicular to each other, and
wherein said positive and negative electrodes are bow-shaped backwards against said sites.

2. Hybridization equipment in accordance with any of claims 1, wherein a direction of moving said biopolymers is changed during hybridization of said biopolymers by changing over directions of said electric and magnetic fields.

3. Hybridization equipment in accordance with claim 2, wherein said positive and negative electrodes are attached to said substrate directly, or indirectly through fixing members so that said sites are sandwiched between said electrodes.

4. Hybridization equipment in accordance with claim 2, wherein magnets are used or a coil is used for said magnetic field generating means.

5. Hybridization equipment in accordance with claim 4, wherein said biochip substrate is placed inside said coil if said coil is employed for said magnetic field generating means.

6. Hybridization equipment in accordance with claim 2, wherein a DC power supply or an AC power supply is used as the power supply to apply a voltage to said electrodes.

7. Hybridization equipment in accordance with claim 2, wherein said fluid is liquid or gel.

8. Hybridization equipment in accordance with claim 2, wherein said substrate is formed with a plate or wire or mesh.

* * * * *